(12) United States Patent
Hamann et al.

(10) Patent No.: US 9,109,989 B2
(45) Date of Patent: Aug. 18, 2015

(54) CORROSION DETECTOR APPARATUS FOR UNIVERSAL ASSESSMENT OF POLLUTION IN DATA CENTERS

(75) Inventors: Hendrik F. Hamann, Yorktown Heights, NY (US); Levente I. Klein, Tuckahoe, NY (US)

(73) Assignee: International Business Machines Corporation, Armonk, NY (US)

(*) Notice: Subject to any disclaimer, the term of this patent is extended or adjusted under 35 U.S.C. 154(b) by 625 days.

(21) Appl. No.: 13/439,514

(22) Filed: Apr. 4, 2012

(65) Prior Publication Data

US 2013/0265064 A1 Oct. 10, 2013

(51) Int. Cl.
*G01R 27/08* (2006.01)
*G01N 17/04* (2006.01)

(52) U.S. Cl.
CPC ............................ *G01N 17/04* (2013.01)

(58) Field of Classification Search
CPC ................................ G01R 27/08; G01R 17/04
USPC ......... 324/700–713, 600, 315, 431, 441, 224, 324/750.03–750.07, 750.28, 670, 685; 73/579, 600, 623, 86, 597, 598, 618, 73/630, 67.859; 205/775.5, 775
See application file for complete search history.

(56) References Cited

U.S. PATENT DOCUMENTS

| | | | |
|---|---|---|---|
| 3,578,409 A | 5/1971 | Silverman et al. | |
| 4,217,544 A * | 8/1980 | Schmidt | 324/721 |
| 4,587,479 A | 5/1986 | Rhoades et al. | |
| 4,689,472 A * | 8/1987 | Singleton et al. | 392/405 |
| 4,869,874 A | 9/1989 | Falat | |
| 5,208,162 A | 5/1993 | Osborne et al. | |
| 5,627,749 A | 5/1997 | Waterman et al. | |
| 5,994,144 A | 11/1999 | Nakajima et al. | |
| 6,628,111 B2 | 9/2003 | Shapiro et al. | |
| 7,430,893 B2 | 10/2008 | Grayfer et al. | |

OTHER PUBLICATIONS

Ashrae Technical Committee, (Tc) 9.9, "Gaseous and Particulate Contamination Guidelines for Data Centers", White Paper, 2009, pp. 1-13.

(Continued)

*Primary Examiner* — Melissa Koval
*Assistant Examiner* — Trung Nguyen
(74) *Attorney, Agent, or Firm* — Scully, Scott, Murphy & Presser, P.C.; Vazken Alexanian

(57) ABSTRACT

A compact corrosion measurement apparatus and system includes an air fan, a corrosion sensor, a temperature sensor, a humidity sensor, a heater element, and an air flow sensor all under control to monitor and maintain constant air parameters in an environment and minimize environmental fluctuations around the corrosion sensor to overcome the variation commonly encountered in corrosion rate measurement. The corrosion measurement apparatus includes a structure providing an enclosure within which are located the sensors. Constant air flow and temperature is maintained within the enclosure where the corrosion sensor is located by integrating a variable speed air fan and a heater with the corresponding feedback loop control. Temperature and air flow control loops ensure that corrosivity is measured under similar conditions in different facilities offering a general reference point that allow a one to one comparison between facilities with similar or different pollution levels.

27 Claims, 7 Drawing Sheets

(56) References Cited

OTHER PUBLICATIONS

Klein et al., "Corrosion Management for Data Centers", IBM Research Report, RC24120, Mar. 8, 2011.

Purafil, OnGuard 3000 Atmospheric Corrosion Monitor (OG3), "Atmospheric Corrosion Monitor Protects Sensitive Electronics from Corrosive Gases", Oct. 2, 2006, http://www.purafil.com/literature/onguard_3000_industrial.pdf, downloaded Apr. 15, 2011.

* cited by examiner

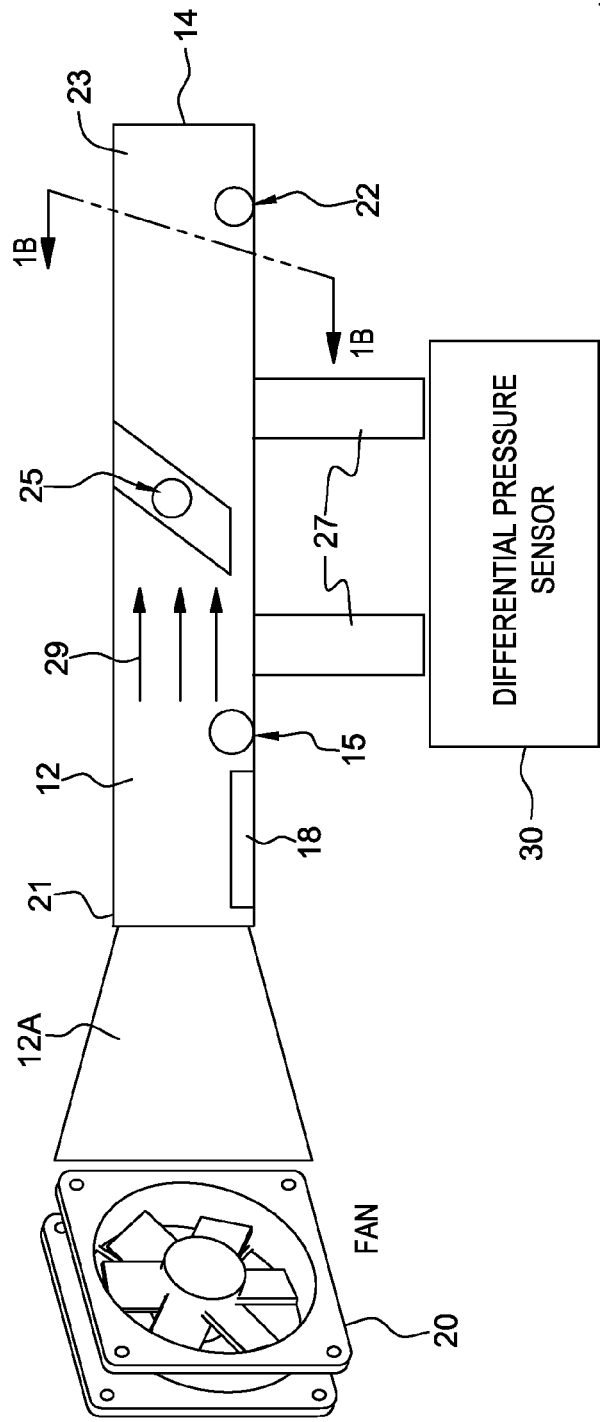
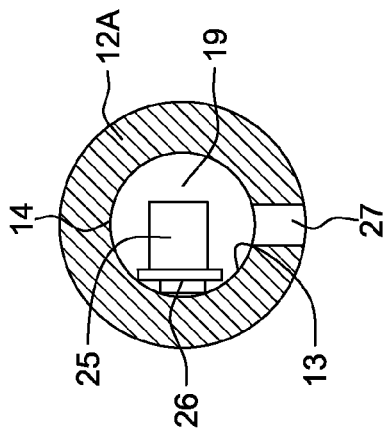
FIG. 1A
FIG. 1B

CORROSION DETECTOR APPARATUS FOR UNIVERSAL ASSESSMENT OF POLLUTION IN DATA CENTERS

GOVERNMENT CONTRACT

This disclosure was made with Government support under Contract No.: DE-EE0002897 awarded by the United States Department of Energy. The Government has certain rights in this disclosure.

BACKGROUND

The present disclosure generally relates to a device, system and method for minimizing environmental fluctuations around a corrosion sensor to overcome the variation commonly encountered in corrosion rate measurements and assess the true contamination level in data centers.

Corrosion is determined by the synergistic effects of "air" parameters such as temperature, humidity, air flow (speed), and gaseous contamination concentrations. Any of the above mentioned "air" parameters will affect the corrosion rate of certain metals, and as a result, measurement of the corrosion rate can vary depending on the location of the measurement and the environment that a corrosion sensor will see.

For example, corrosion sensors positioned at the outlet of an air conditioning unit may not detect the full extent of corrosion as the temperature is too low to trigger the corrosion, but at higher temperature a finite corrosion rate may be detected. Depending on the measurement location, either no corrosion or significant corrosion could be measured in the same facility.

Air parameters like temperature, humidity and air flow can influence corrosion in polluted atmospheres resulting in corrosion rates that can differ by more than a factor of five (5) or larger in the same facility.

The proliferation and spread of facilities such as information technology (IT) Data Centers (DC) into geographies with higher levels of atmospheric contamination and the use of air-side cooling within data centers require more attention towards air quality management as a data center encounters large variation of temperature, air flow and humidity over short distances. Besides temperature, humidity, and air flow, the concentration of gaseous contamination can also affect the corrosion rate in data centers. One concern of air side economization is the possibility of unintentional introduction in a facility of a large amount of gaseous and particulate pollutants potentially leading to more failures and outages of the IT equipment. That is, IT equipment operated at high temperatures and increased humidity combined with high level of air contamination can lead to enhanced corrosion risk in data centers.

Two types of contamination that have been identified to impose risk on IT equipment include particulates and gaseous contaminations. Recent investigation of the particulate contamination levels in data centers established that proper filtering can reduce the concentrations to acceptable levels. However, for gaseous contamination monitoring, the American Society of Heating, Refrigerating and Air-Conditioning Engineers (ASHRAE) publication [see, ASHRAE Whitepaper, "Gaseous and Particulate Contamination Guidelines for Data Centers", 2009] states that reactivity should be measured both for copper and for silver. Currently, the study recommends that copper and silver corrosion rates should be maintained less than 300 Å/month for a non-contaminated environment. Furthermore the ASHRAE publication suggests that in situations where atmospheric contamination is high, proper filtration should be used to reduce the corrosion levels below 300 Å/month.

The ASHRAE guidelines are designed to minimize the physical failure risks of the IT equipment, while achieving higher energy efficiency. Certain limitations are set for temperature or relative humidity levels to reduce condensation or overheating risk of the IT equipment. For example, it is suggested that humidity levels below 20% can increase the probability of electrostatic discharge (ESD) and implicitly the failure of integrated circuit components. High humidity levels (above 70%) may increase the probability of Printed Circuit Board (PCB) delamination, anodic filament growth, zinc whisker growth and corrosion.

Standard industrial methods to measure corrosion rely on exposing metal (silver and copper) coupons to a polluted atmosphere and collecting the coupons after at least a one month period of such exposure. For field deployed copper and silver coupons, it has been observed that the corroded surface shows spatial variations across the surface depending on the direction of air flow, temperature, surface preparation and humidity. Even coupons which hang near each other will have different corrosion product thickness and variation across their surfaces indicating that the local environment has a large impact on the corrosion formation.

The desire of operating data centers (DCs) more energy efficient has resulted in two trends: (1) environmental operating parameters for IT equipment have been significantly expanded, and (2) air side economizers are increasingly used to offset cooling energy consumption, which can be substantial fraction of the total DC power. These two trends can have significant implications for the corrosion risk of a DC.

While filtering of the outside air, both for particulate and gaseous contamination, can mitigate air contamination in data centers, implementing a facility wide air quality monitoring system promises the safe use of air-side economizers and would establish appropriate filtering.

BRIEF SUMMARY

The present disclosure provides a high sensitivity real-time corrosion measurement apparatus, system and method for measuring corrosion rates based on real time corrosion sensing in an environment.

More specifically, a high sensitivity real-time corrosion measurement apparatus, system and method for measuring corrosion rates based on real time corrosion sensing in multiple environments and comparing the corrosion rates in different environments while maintaining the reliability of the comparison method are provided.

The corrosion measurement apparatus of the present disclosure includes one or more highly sensitive real time corrosion sensor device(s) for sampling corrosion under similar (common) environmental conditions. Deployment of such devices in a same facility or different facilities under similar (common) environmental conditions enables the comparison of corrosion rates between facilities with similar or different pollution levels.

According to one embodiment, a corrosion measurement apparatus is provided that includes: a structure forming an enclosure having a first end and a second end; a corrosion sensor device located within the enclosure; a first sensor device located within the enclosure for determining a respective air flow value within the enclosure; a second sensor device located within the enclosure for determining an air temperature value within the enclosure; a third sensor device located within the enclosure for determining an air humidity value within the enclosure; a fan device located at the first end of the structure; a heating device located within the enclosure; and a control device operatively connected with the fan device and heating device for receiving real-time air flow, air temperature and air humidity values, and, responsive to the values, the control device generating one or more control signals for modifying operation of at least one of the heating device or fan device, to provide a target uniform temperature and a target air flow within the enclosure while obtaining a corrosion rate measurement via the corrosion sensor device.

According to another embodiment, a corrosion measurement method in a corrosive atmospheric environment is provided. The method includes: providing a corrosion measurement apparatus having a structure forming an enclosure having first and second ends, the apparatus further comprising: a corrosion sensor device located within the enclosure; a first sensor device located within the enclosure for determining a respective air flow value within the enclosure; a second sensor device located within the enclosure for determining an air temperature value within the enclosure; a third sensor device located within the enclosure for determining the air relative humidity value within the enclosure, a fan device located at a first end of the structure; a heating device located within the enclosure; and a control device operatively connected with the fan device and heating device for receiving real-time air flow, air temperature and air humidity values; generating, by the control device, responsive to the values, one or more control signals for modifying operation of one or more of the heating device or the fan device to achieve a target air temperature and a target uniform air flow within the enclosure; and, obtaining, via the corrosion sensor device, a corrosion rate measurement while the target air temperature and a target uniform air flow values are achieved within the enclosure.

According to yet another embodiment, a method for real-time corrosion measurement in corrosive atmospheric environments is provided. The method includes: providing a plurality of real-time corrosion measurement apparatuses each apparatus at one or more environments, each corrosion measurement apparatus comprising: a structure forming an enclosure having a first end and a second end; a corrosion sensor device mounted within the enclosure; a first sensor device located within the enclosure for determining a respective air flow value within the enclosure; a second sensor device located within the enclosure for determining an air temperature value within the enclosure; a third sensor device located within the enclosure for determining a relative humidity value within the enclosure, a fan device located at the first end of the structure; a heating device located within the enclosure; and a control device operatively connected with the fan device and heating device to receive real-time air flow, air temperature and air humidity values from the enclosure, and generate, responsive to the values, one or more control signals for modifying operation of one or more of the heating device or the fan device; providing, using the control signals at each respective device of the plurality of corrosion detection devices, a common condition of a target air flow, target air humidity, and target air temperature values within the enclosure of each measurement apparatus at each the one or more environments; and, obtaining, via the corrosion sensor device of each measurement apparatus, a corrosion rate measurement while the common condition is provided within the enclosure at each respective one or more environments.

A computer program product is provided for performing operations for real-time corrosion measurement in corrosive atmospheric environments. The computer program product includes a storage medium readable by a processing circuit and storing instructions run by the processing circuit for running a method. The method is the same as listed above.

BRIEF DESCRIPTION OF THE DRAWINGS

FIG. 1A depicts a corrosion measurement apparatus 10 according to one embodiment;

FIG. 1B is a cross sectional view of apparatus 10 taken along line 1B-1B of FIG. 1A;

DETAILED DESCRIPTION

Figure 2:
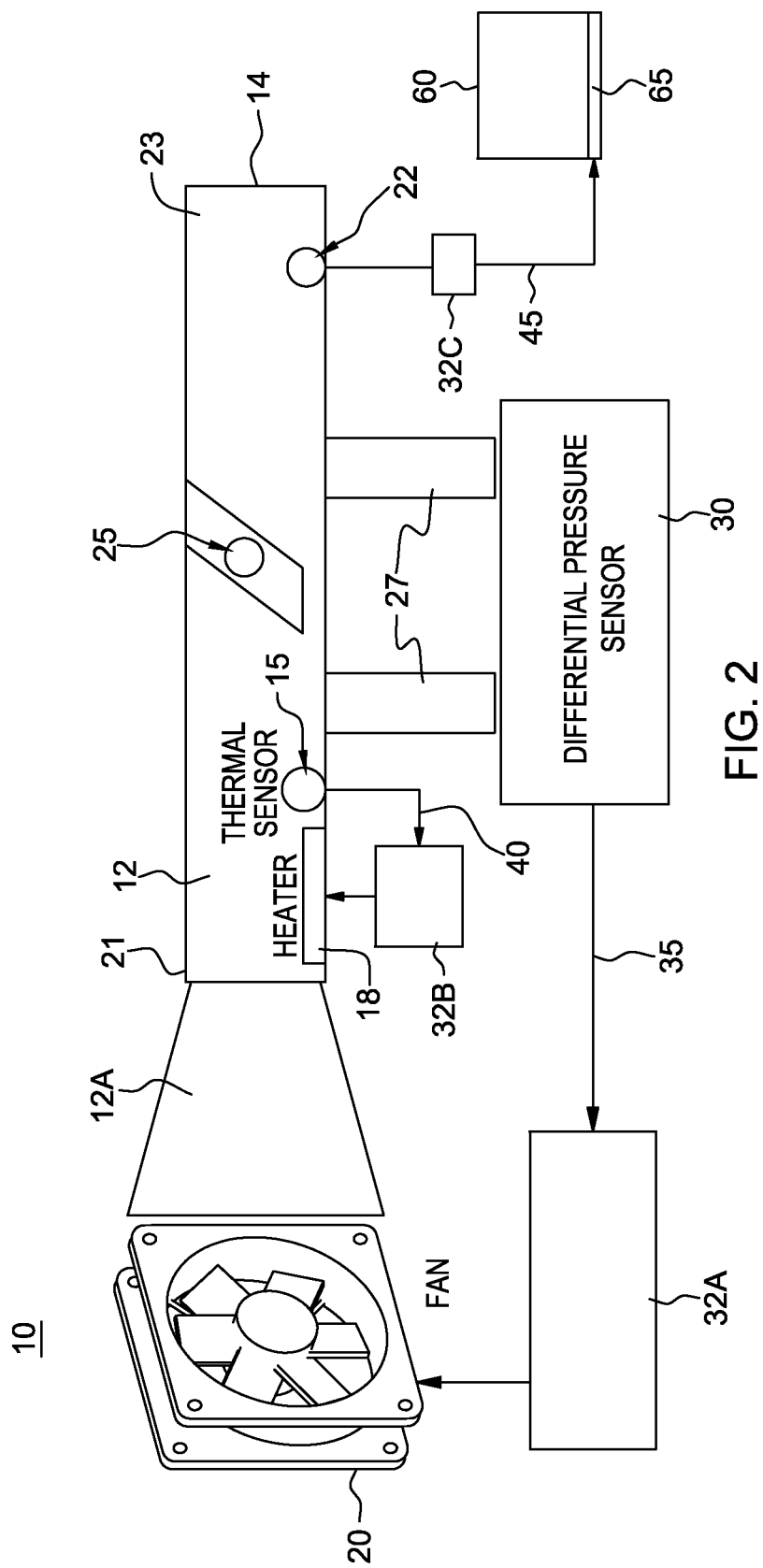
FIG. 2 depicts the corrosion measurement apparatus 10 of FIG. 1A including feedback control devices providing respective feedback loops for adjusting the temperature and air flow parameters for the controlled environment according to one embodiment.

A high sensitivity real-time corrosion measurement apparatus, system and method for measuring corrosion rates based on real time corrosion sensing in one or more environments are now described.

As referred to herein, "air parameters" includes air temperature, air humidity (e.g., relative humidity), and/or air flow (air speed), e.g., in units of air volume/time, and concentration of gaseous contaminants in an environment.

Referring to FIG. 1A, there is depicted a compact corrosion measurement apparatus 10 according to one embodiment of the present disclosure.

As shown in FIG. 1A and in the cross sectional view of FIG. 1B, the corrosion measurement apparatus 10 includes a structure 12 defining an enclosure or housing having a hollowed interior 19, e.g., a tube or pipe structure. The structure 12 has a first end 21 and second end 23. As shown in FIG. 1A, second end 23 includes an opening 14. The structure 12 can be metal, plastic or ceramic material. A corrosion sensor 25 and associated circuitry 26 for corrosion rate measurements is positioned within the enclosure, e.g., on an interior surface 13 of the structure between the two ends. In one embodiment, corrosion sensor 25 is a reactivity monitoring type corrosion sensor 25 and associated circuitry 26 is positioned at or proximate a middle section of the structure 12.

In one embodiment, the corrosion sensor 25 is positioned perpendicular to the main axis of the structure 12, facing a fan that pushes air toward it. In its manufacture, the corrosion sensor 25 may be lowered through a slot (not shown) that is cut in the top of the structure 12. This cut may be subsequently sealed. The detection circuit for corrosion rate calculations can be positioned inside or outside of the structure 12. Further, in one embodiment, a lower limit of the tube diameter is defined by the corrosion sensor device 25 that is positioned inside the structure 12. In this embodiment, sensor device 25 is positioned such that is perpendicular to the air flow and has a laminar flow across it. The structure 12 will be slightly larger than the corrosion sensor to avoid air flow turbulences that may develop near the walls of the structure 12. In one implementation, a structure 12 size that could accommodate the sensor device 25 ranges from 0.1 inch to 1 inch square size.

The corrosion measurement apparatus includes an end portion 12A that is integral with or attached to the enclosure at first end 21 of structure 12, and is of suitable dimension to accommodate attachment of a variable speed fan device 20. In one embodiment, the hollow interior 19 of structure 12 is designed as a tube to ensure a smooth (laminar) flow of air from the fan when activated in the manner disclosed herein. The fan device 20 and end portion 12A positioned at first end 21 of the structure 12 is designed to ensure a laminar air flow 29 within the structure 12 from the first end 21 toward the second end 23 of the structure 12 through opening 14. This flow of air is feedback controlled in a manner as described herein below such that uniform air flow is achieved over the interior wall surface, and particularly a uniform air flow is achieved at the positioned corrosion sensor surface. In one embodiment, the corrosion sensor device 25 is positioned perpendicularly with respect to the interior surface and with respect to the air flow. Alternately, the sensor device 25 can be positioned to have air flowing parallel with sensor surface.

In one embodiment, the air flow parameter within structure 12 can be measured using a differential pressure method, such as based on Pitot tube principle for example, or using an air flow sensor. Alternately, a differential pressure sensor 30 is used.

FIG. 1A further shows an embodiment of a corrosion measurement apparatus 10 employing a differential pressure sensor 30. In this embodiment, two additional hollow (e.g., tube or pipe) structures 27 operatively attach to the structure 12 through the wall of the structure 12 and extend outward therefrom. The hollow interiors 39 of each hollow structure 27 communicate with the hollow interior 19 of structure 12. As shown in FIG. 1A, the differential pressure sensor 30 is situated between or connected to the two hollow structures 27 that are operatively attached to the wall. Each respective output 27A at the other end of each hollow structure connects with the differential pressure sensor 30 to measure the air flow within the interior 19 of structure 12. It is understood that if an air flow sensor is used, that air flow sensor is placed directly in the interior of structure 12.

Thus, in the embodiment of the corrosion measurement apparatus 10 in FIG. 1A, the variable speed fan 20 positioned at end portion 12A at first end 21 of structure 12 provides a flow of air in the structure 12 at a speed that is real-time adjustable by varying the power supply voltage (or current) to the fan that controls the rotation speed of the fan. As shown in FIG. 2, a feedback mechanism under control of a controller device 32A can adjust the fan speed such that air flow is maintained at a certain air flow set point. The real-time air flow sensor or differential pressure sensor reading output signal 35 constitutes the control signal for the feedback loop.

Further in the embodiment of corrosion measurement apparatus 10 shown in FIG. 1A and FIG. 2, a humidity sensor device 22 and a temperature sensor device 15 can be situated in the interior of structure 12 to measure the air parameters of humidity and temperature, respectively. To maintain constant temperature, a heater element 18 can be mounted inside the structure 12 whose temperature can be adjusted in real-time to achieve a set air temperature. For example, if the temperature sensor 15 provides output indicating that the temperature is below the desired value, a controller 32B receives either via hard-wired or wireless communication that output and responsively generates a feedback control signal 40 to activate the heater element 18 to raise the temperature to the desired set condition. In one embodiment, the temperature sensor 15 is placed behind the heater element 15 such that air speed/volume and temperature is constant within the structure 12.

In another implementation, the heater element 15 may be attached to the back of the corrosion sensor device 25 and adjusted to maintain the corrosion sensor device 25 at a constant temperature.

In a further embodiment, to maintain a constant relative humidity level within the device, the humidity sensor device 22 is controlled in real-time to achieve a set air moisture level. A controller 32C receives real-time output sensor signals either via hard-wired or wireless communication from the humidity sensor device 22 and generates a feedback control signal 45 to activate a humidifier element 60 which may be a humidifier or like device to raise the moisture level in the ambient air to a desired set condition. In one embodiment, the humidifier element 60 includes a small container of water and a heater element 65, different from heater element 18, that is located at the bottom of the container. Alternately, the humidifier element 60 may be provided within the enclosure structure 12. The temperature of the heater element 65 can be increased to warm the water in the container and consequently to increase the water vapor pressure that is mixed with the air in the structure 12 to achieve a desired humidity level in the structure 12 that contains the corrosion sensor device 25. A feedback control loop 45 adjusts the temperature of the heater element 65 based on the desired relative humidity level for corrosion measurement within the structure 12. Alternately, humidifier element 60 may include a de-humidifier or like device to reduce the moisture level in the ambient air to a desired set condition. For example, feedback control loop 45 may be used to adjust the heater element 18 temperature within the structure 12 to the desired set relative humidity level for corrosion measurement within the structure.

In this embodiment, an apparatus may be located at the first end 21 of the structure 12 that includes the integrated heater element 18 that would control the vapor pressure within the structure 12, or, a heater element 65 attached to the apparatus whose temperature can be controlled to adjust the humidity level of the air flowing through the structure 12.

In one embodiment, corrosion sensor device 25 includes a clean metal surface exposed to the contaminated atmosphere such that the growth rate of contamination product is measured. In one embodiment, corrosion sensor device 25 is a sensitive atmospheric contamination sensor with a corrosion rate sensitivity of 1 Å/day, for example, and a sensor lifetime of over 5 years. In one embodiment, a corrosion sensor and associated circuitry is employed such as described in commonly-owned, co-pending U.S. patent application Ser. No. 12/854,416 entitled "CORROSION SENSORS", the whole disclosure and content of which is incorporated by reference as if fully set forth herein.

For example, the corrosion sensor device 25 includes thin metal film structures (e.g., copper or silver, or any other metal desired for corrosion monitoring) deposited on a glass or silicon substrate surface. The corrosion is measured by monitoring the change in resistance of the metal film element. The width of the metal film is much larger than the film thickness assuring that any change in resistance is fully due to film thickness change. Once the metal film is exposed to a corrosive environment, the silver (or copper) film becomes transformed into non-conductive corrosion products like $Ag_2S$, $Cu_2O$, $Cu_2S$, etc. It is understood that other corrosion products may be detected using a device that is dependent on what pollution the sensor is exposed to. This change in chemical composition of the film results in a change in film thickness and an increased resistance of the thin film structure. The resistance change is converted to film thickness loss and the change over a period of time gives the corrosion rate.

In an alternate embodiment, the metal films (e.g., silver and copper or any metallic material) sensors are located on the same substrate or on different substrates such that corrosion rates for both metals are investigated simultaneously under similar environmental conditions.

In one embodiment, corrosion sensor detection includes connected circuitry to measure and obtain real-time corrosion sensor readings. In one embodiment, the corrosion rate determining sensor circuitry includes a Wheatstone bridge or like bridge measurement circuitry where the exposed silver and copper film elements are resistors of the bridge arm such that small changes in resistance can be detected is as described in commonly-owned, co-pending U.S. patent application Ser. No. 12/854,416.

In one embodiment, control devices 32A and 32B and associated circuitry may be located external to the structure 12 and may include a proportional-integral-derivative controller (PID) feedback loop controller implemented to adjust the respective air flow, relative humidity, and temperature for controlled environment. Alternately, control devices 32A and 32B and associated circuitry may be located internal to the structure 12 implementing sensor feedback loop controller to adjust the respective air flow, relative humidity, and temperature for the internal structure 12 environment. FIG. 2 shows first PID controller 32A connecting both the differential pressure sensor device 30 and the fan device 20 and programmed to maintain a constant air flow rate. Second PID controller 32B connects both the temperature sensor device 15 and the heater element 18 and is programmed to control the temperature within the interior of structure 12. As known, proportional-integral-derivative controller (PID controller) provides a control loop feedback mechanism—that calculates an "error" value as the difference between a measured process variable and a desired set point. The controller attempts to minimize the error by adjusting the process control inputs. The PID controller calculation (algorithm) involves three separate constant parameters: the proportional, the integral and derivative values, denoted P, I, and D (See, e.g., http://en.wikipedia.org/wiki/PID_controller). Using heuristics, these values can be interpreted in terms of time: P depends on the present error, I on the accumulation of past errors, and D is a prediction of future errors, based on current rate of change. The weighted sum of these three actions is used to adjust the process being controlled: e.g., the amount of current to the fan element, or the amount of power supplied to the heating element. It is understood that controller devices 32A, 32B may be any type of programmed control device for adjusting the air parameters, e.g., P-I controller, or Optimal control: Model Predictive control; Robust Control; and Adaptive control methods.

A control method 100 for continuous real-time control of temperature, humidity and air flow parameters within structure 12 at a single location (e.g., data center) is now described. In one embodiment, control method 100 is programmed in each controller device, e.g., PID devices 32A, 32B, as now described with respect to FIGS. 3A and 3B. It is assumed a supervisory computer or controller (not shown) that interfaces with each of the individual controllers 32A, 32B may be provided for device programming purposes, e.g., to set or reset an air parameter value set point for the controller of the device. The method is applicable to each of a plurality of corrosion measurement apparatuses 10 that may be situated in a data center to ensure substantially identical environmental conditions for corrosion sensor device 25 measurements at each apparatus 10. Multiple PID controlled devices can be active at the same time or independently, and their operation is optimized to achieve the expected environmental conditions in the structure 12.

Figure 3A:
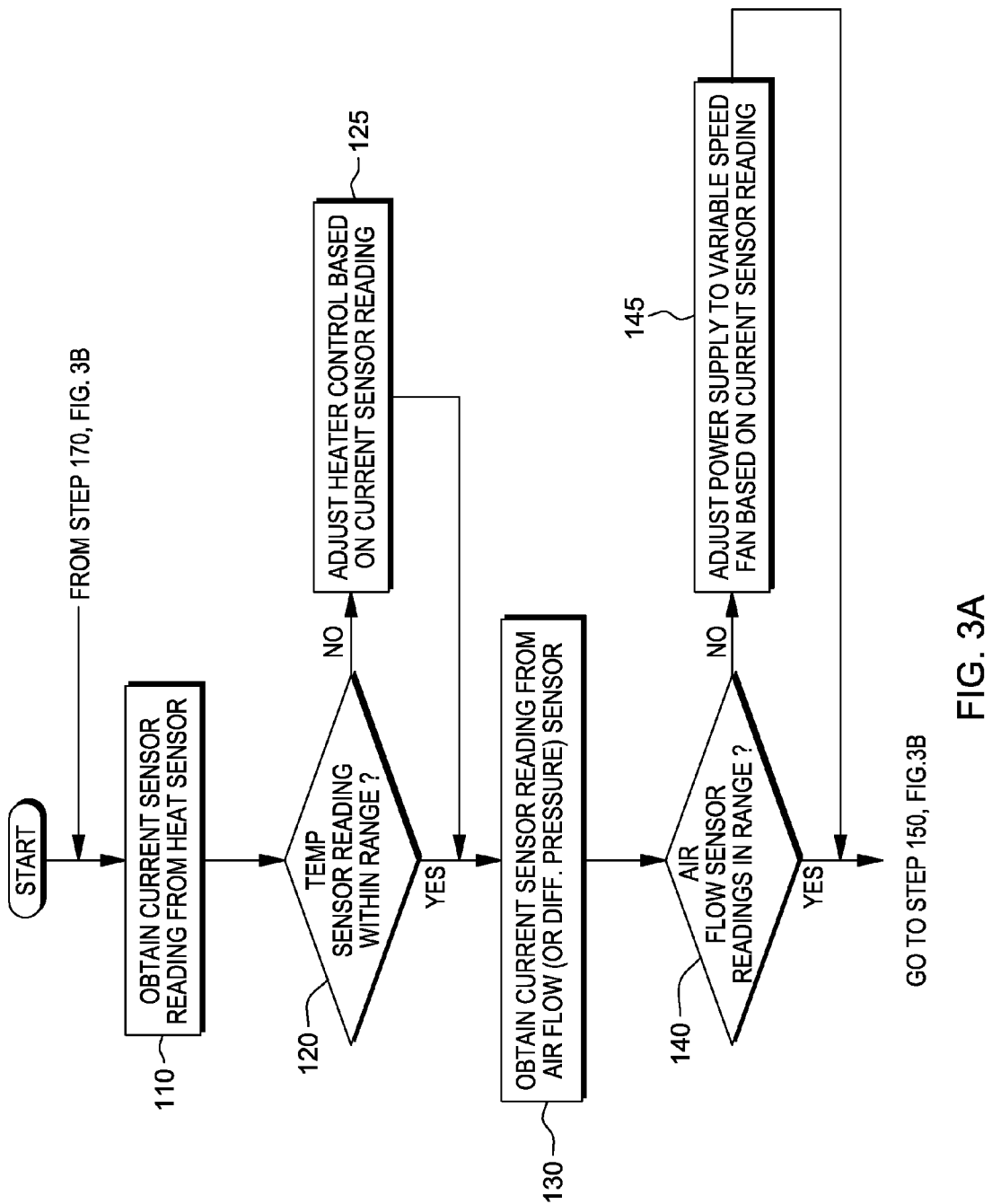
FIGS. 3A and 3B depict a flow chart showing a sequence of steps 100 employed by the feedback control device(s) to control and maintain target air parameters for corrosion rate measurement.

As shown in FIG. 3A, at 110, there is represented a step of obtaining a current temperature reading from heat sensor 15, and determining at 120 whether the current temperature sensor reading is within range. If the current temperature sensor device reading is below the programmed set point, the heater element 18 is activated to control temperature at corrosion sensor device 25 within the structure 12 based on current sensor reading and operation continues at step 130. Otherwise, if the current temperature sensor reading is within temperature set point range, the process continues to step 130. At 130, there is represented a step of obtaining a current air flow (or differential pressure) value from, e.g., differential pressure sensor 30, and determining at 140 whether the current air flow value (differential pressure sensor reading) is within a programmed range. If the current differential pressure sensor reading is outside of the programmed set point, the variable speed fan device 20 is activated at 145 to control air flow speed at corrosion sensor device 25 within the structure 12 based on current air flow sensor reading and operation continues at step 150, FIG. 3B. Otherwise, if the current differential pressure sensor reading is within temperature set point range, the process continues to step 150, FIG. 3B. In one embodiment, air flow velocity may range anywhere from between 0.001 m/sec up to 10 m/s as velocity.

Figure 3B:
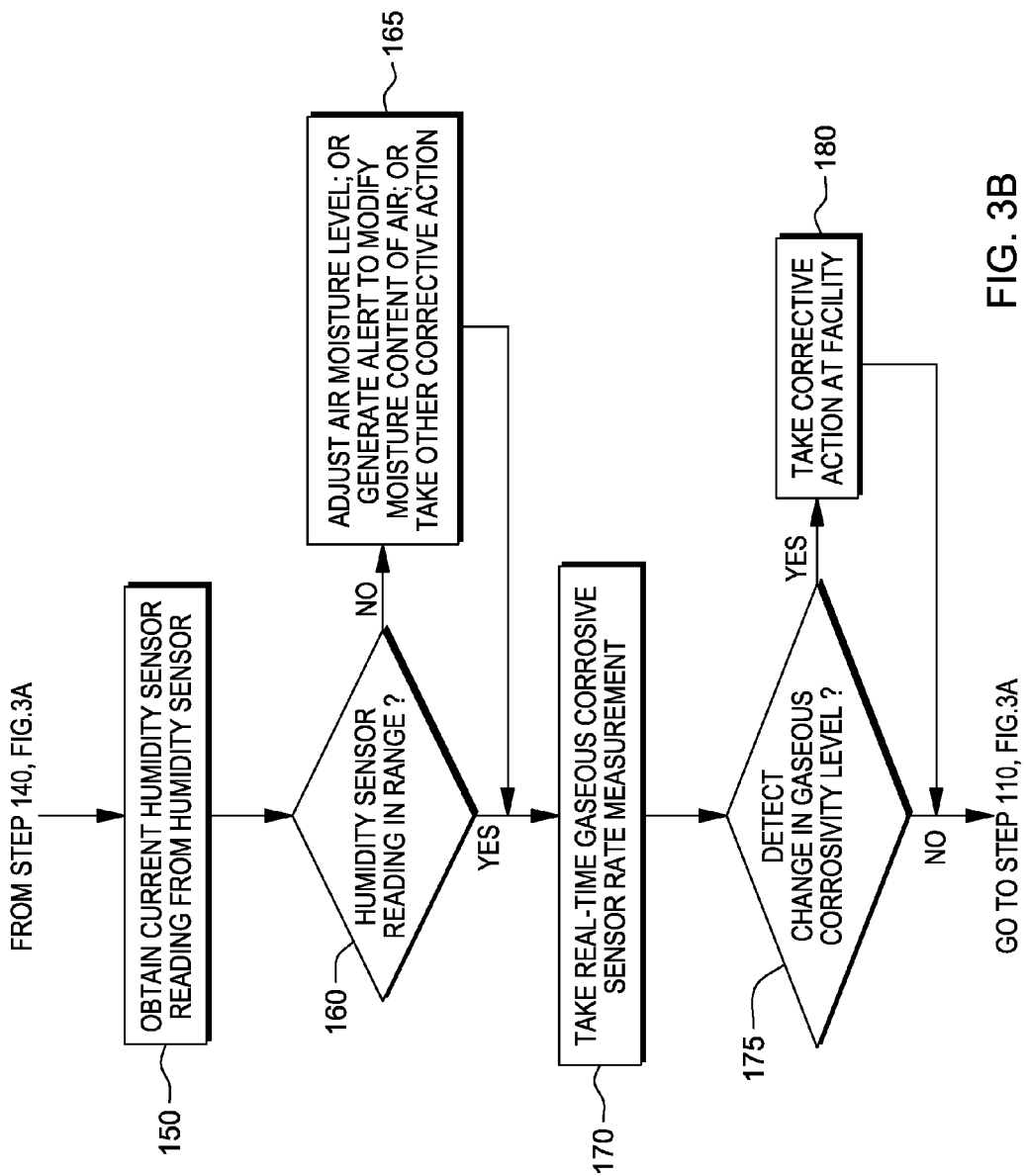

Continuing at 150, FIG. 3B, the method may further include obtaining a current relative humidity sensor reading from humidity sensor device 22, and determining at 160 whether the current relative humidity sensor reading is within a programmed range. If the current relative humidity sensor reading is outside of the programmed set point, an alert or alarm signal (e.g., audio and/or visual indicator) may be generated by the device at 165 in order to alert the facility operators that the moisture content of the ambient air is not within acceptable limits for the intended operation. In an alternate embodiment (not shown), a wired or wireless alarm signal may be generated by the apparatus 10 that is communicated to and directly received by the facility operators to indicate a sensed out of range humidity condition.

Further, as described herein with respect to FIG. 1B, control device 32C associated with the device may be implemented to perform real-time corrective actions to adjust the moisture content or other air parameters of the air within interior 19 of the corrosion measurement apparatus 10 responsive to the current sensed humidity condition and signals obtained from the humidity sensor device 22, e.g., by adjusting heating element 18, to achieve a target humidity or air moisture parameter value.

In a further embodiment, control device 32C associated with the device may be implemented to perform real-time corrective actions to adjust the moisture content or other air parameters of the ambient air within the facility responsive to the current sensed humidity condition obtained from the humidity sensor device 22, e.g., by adjusting humidifier element 60 (or a dehumidifier) to achieve a target humidity or air moisture parameter value.

Continuing, in FIG. 3B, whether a sensed relative humidity range is determined within set point limits at 160 or, after taking a corrective action(s) to address out of range sensed humidity reading at 165, the process proceeds to 170 where the actual corrosion rate sensor reading is obtained. For data centers with air-side economizers, it is necessary to have real-time monitoring to react quickly to events outside the data centers that may release corrosive gases which may flow into the data centers. The possible corrosion sensor implementations could be either a quartz crystal microbalance, or a resistive method of measuring the resistance change of the metal thin films. Both these methods may be used to measure cumulative corrosion over an exposure time, e.g., to comply with acceptable corrosivity rate limits as recommended by ASHRAE. For example, in certain environments that are considered mildly corrosive, copper and silver metal film corrosion rates should be maintained at less than 300 Å/month. In one embodiment, the corrosion rates can range from anywhere between 10 Å/month up to 10000 Å/month within the structure interior, where Å is Angstrom units.

Thus, in the example embodiment the change in resistance of the metal film is used to measure the corrosion rate. The rate relates to how fast the metal film is transformed electrochemically. After taking a corrosivity rate measurement reading, it is determined at 175 whether a change in corrosivity rate level has been detected. If so, depending on the amount of change detected, the process proceeds to 180 to take any corrective action. For example, substantial changes in gaseous corrosivity detected may allow preventive measures to be taken at 180, such as shutting off outside air carrying pollutants from entering the facility (data center). In one embodiment, a "substantial" change or "delta" to trigger such action may be detection of any corrosion rate larger than 300 Å/month as stated by ASHRAE. Whether corrective action at 180 is taken or not, the operation automatically returns to step 110, FIG. 3A for a next current of sensor readings. The steps described in FIGS. 3A and 3B repeat for real-time or near real-time (periodic) monitoring.

Figure 4:
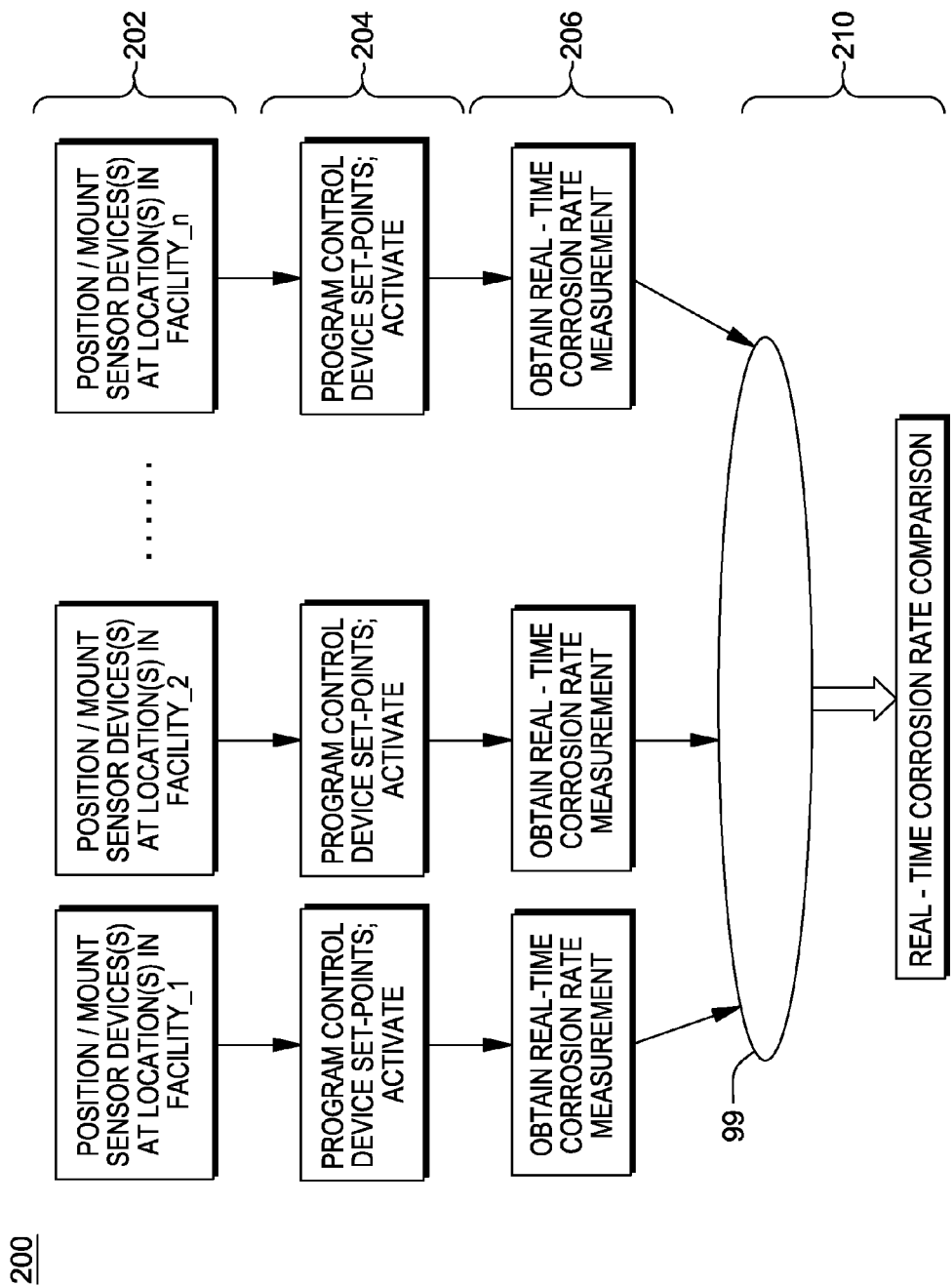
FIG. 4 depicts a corrosion measurement method 200 including one or more corrosion measurement apparatuses 10 activated at common locations in multiple data centers in one embodiment.

The corrosion measurement apparatus 10 can be deployed in plural data centers in different geographical areas where different levels of pollution are expected. To reliably compare the corrosion rate, the commonality of the way to measure corrosion rate in different places is achieved in order to minimize the air parameters effects on the corrosion rate. Thus, as shown in FIG. 4, in an example embodiment, a corrosion rate measurement method 200 includes at 202 positioning one or more corrosion measurement apparatuses 10 at common locations in a facility, e.g., a data center(s), such as facilities labeled facility_1, facility_2, . . . , facility_n. Each facility may be at different geographic locations, or, the devices may be located in different facilities at a single geographic location (e.g., within a single building). Then, either in parallel, or individually, at 204, each of the controllers, e.g., 32A, 32B and 32C for each of the sensor devices within the structure 12 are programmed with the desired air parameter set points. Thus, for example, a corrosion measurement apparatus at each facility at different geographic locations, or, at different facilities within a single location, is programmed and activated to achieve identical microenvironment conditions within the structure 12 of each apparatus 10. As shown in FIG. 4, each device/controller may be programmed via network communications, e.g., a hard-wired or wireless communications infrastructure, or a combination of both, as shown by network 99 under control of a host computer or control device 400 as described herein with respect to FIG. 6. Continuing at 206, there is represented the step of obtaining real-time corrosion rate measurements from corrosion sensors at each facility_1, facility_2, . . . , facility_n, whether at single or different geographic locations. Then, at 210, via network connections, corrosion rate sensor measurements out of each apparatus 10 are further communicated, e.g., via hard-wired or wireless communications infrastructure, or both, to a host computing device, such as a computing system 400 shown in FIG. 6, that implements algorithms for comparing different corrosion rate levels taken under similar temperature, air flow and humidity microenvironment conditions around the corrosion sensor device 25 of each measurement apparatus. That is, the temperature, relative humidity and air flow control loops will assure that corrosivity is measured under similar conditions in different facilities and environments (wither at same or different geographic locations) thus offering general reference points that allow a one to one comparison between facilities with similar or different pollution levels. One application implements a method to compare corrosion rates within a facility or multiple facilities. Based on the comparisons, corrective action may be taken such as modifying a facility to address corrosion. As described in commonly-owned, co-pending U.S. patent application Ser. No. 13,222, 953, entitled "METHODS AND APPARATUS FOR MANAGING CORROSION IN BUILDINGS", the whole contents and disclosure of which is incorporated by reference as if fully set forth herein, this may include relocating or regrouping equipment at a location(s), or selectively modifying filter settings at one or more locations, for example.

Figure 5:
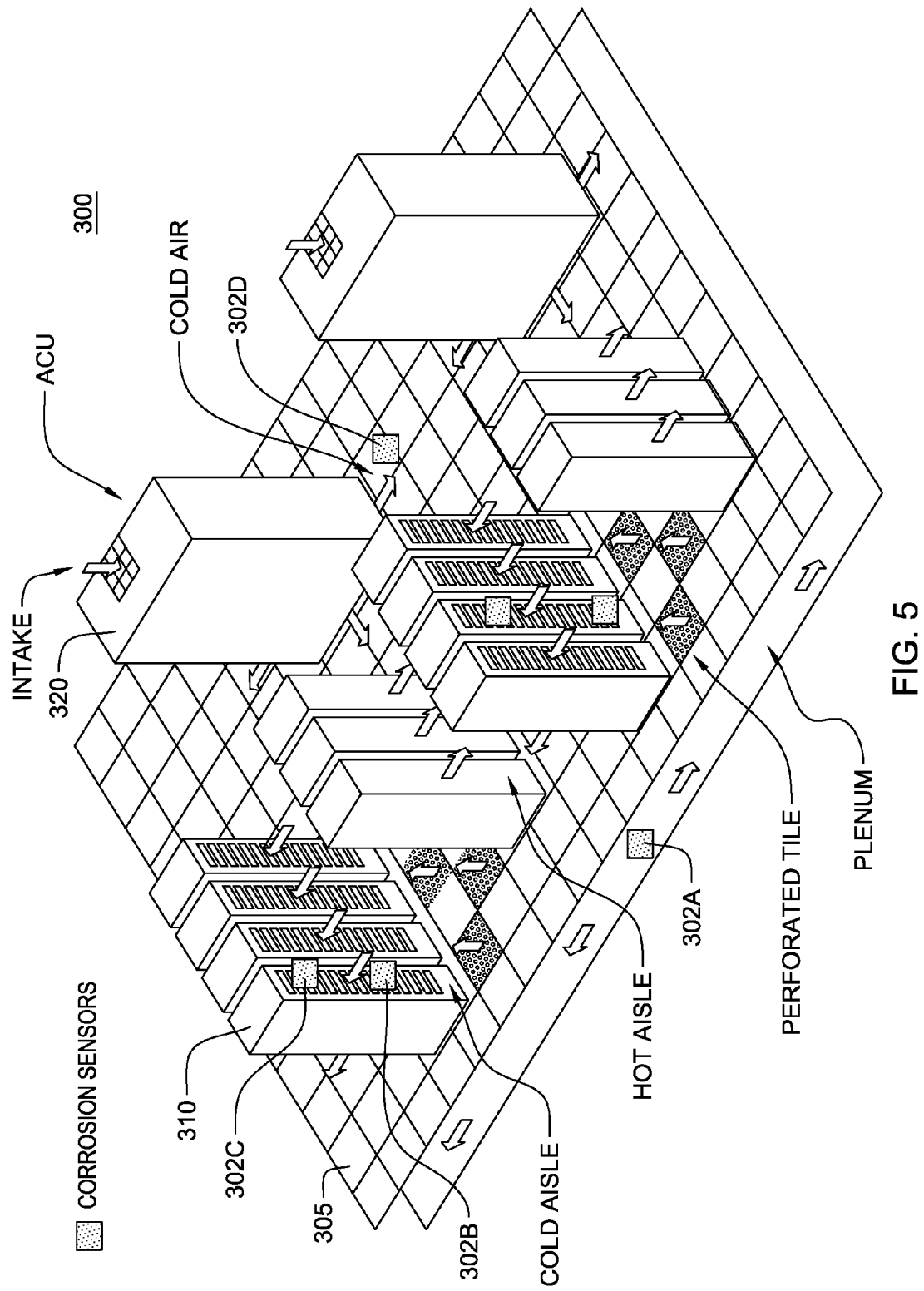
FIG. 5 depicts location of corrosion measurement apparatuses at a facility such as a data center; and, FIG. 6 illustrates an exemplary computing system 400 configured for monitoring corrosion rate measurements at the one or more data centers.

In one embodiment, as shown in FIG. 5, corrosion measuring devices 10 may be located at a facility such as a data center 300 operating multiple computing devices such as IT (information technology) equipment, databases, servers, server racks, air coolers, etc. FIG. 5 shows example locations 302 where devices 10 may be located in a data center 300 for each one or more centers being monitored in the method of FIG. 4. For example, in a non-limiting example, device/sensor placement may be at a location 302A under a raised floor 305 and in front of computing system server racks 310, e.g., at locations 302B and 302C corresponding to heights of about 0.5 m and 1 m. In one embodiment, devices 10 including real-time silver corrosion sensors may be placed in a data center with a raised floor that utilize air cooling. A device/sensor may be mounted at a location 302D proximate the outlet of air conditioning units (ACUs) 320, or in front of computer racks 310, e.g., at 0.1 m above the ground, at a height of 1 m front of rack and at a height of 2 m front of rack.

As pollution and air contamination have spatial and temporal variations, these variations are considered when outside air may be used for DC cooling purposes. The air contamination could be measured both for the indoor and outdoor air to establish when the outdoor air meets the required specifications to be used for air side economization.

In a further embodiment, for certain periods of equipment operation, data centers are to maintain their environment within a recommended envelope. Exceeding the recommended limits for short periods of time may not be a problem, but running near the allowable limits for months could result in increased reliability issues. In one embodiment, data centers are operated according an operating envelope that is specified as acceptable to all IT manufacturers, such that operation within this envelope will not compromise overall reliability of the IT equipment. Thus, programmed set points for temperature, humidity and air flow for apparatus 10 may be governed according to ASHRAE recommended environmental parameters for data center operations (see, http://www.eni.com/green-data-center/it_IT/static/pdf/ASHRAE_1.pdf) where, for example, temperature and relative humidity in the microenvironment may be set according to Table 1 as follows:

TABLE 1

| ASHRAE recommendations | IT equipment environment (2008) |
|---|---|
| Low end temperature | 18° C. |
| High end temperature | 27° C. |
| Low end moisture | 5.5° C. dew point |
| High end moisture | 60% RH and 15° C. dew point |

Thee ranges may apply to the inlets of all equipment in the data center (except where IT manufacturers specify other ranges). Attention is needed to make sure the appropriate inlet conditions are achieved for the front or air intake part of IT equipment racks. For example, the inlet air temperature in many data centers tends to be warmer at the top portion of racks, particularly if the warm rack exhaust air does not have a direct return path to the air handling units. This warmer air may also affect the relative humidity resulting in lower values at the top portion of the rack.

The automated high sensitivity corrosion rate measurements obtained by corrosion measurement apparatuses 10 employing methods of FIGS. 3A, 3B and 4, enables the development of corrosion management strategies in facilities such as data centers.

With respect to data centers, a corrosion management strategy may be devised to: establish the risk levels for IT equipment operated in contaminated atmosphere and propose strategies to mitigate corrosion effects. Since corrosion is a synergistic result of gaseous contamination, temperature, and humidity variations in data centers, the corrosion has to be analyzed in the context of data center operating conditions.

For example, with corrosion management apparatuses 10 installed both inside the data centers and outdoors, the corrosion management enables real time monitoring of the pollution levels of the outside air for cooling purposes. Such a strategy can prevent polluted air being used for cooling purposes, and enable air side economizer utilization when outdoor contamination levels are low. With contamination (corrosion) sensors distributed in the data center, the continuous monitoring will assure that year long air quality specifications are maintained in the data center including the effectiveness of gaseous filters.

Moreover, corrosion management using corrosion measurement apparatus 10 ensures that corrosivity is measured under similar conditions in different data centers thereby providing general reference points that allow a one to one comparison between facilities with similar or different pollution levels.

Further, a facility wide environmental sensor network and method such as shown in FIGS. 4 and 5, enables early prevention of critical situations for IT equipment operations.

Besides data centers, and corrosion measurement apparatuses 10 employing methods of FIGS. 3A, 3B and 4 may be implemented in facilities including, but not limited to: manufacturing or industrial facilities, e.g., operated for the purpose of manufacturing goods, or facilities such as: museums, a semiconductor fabrication facility, a clean room, or any environment that may have contaminants that cause material corrosion.

Figure 6:
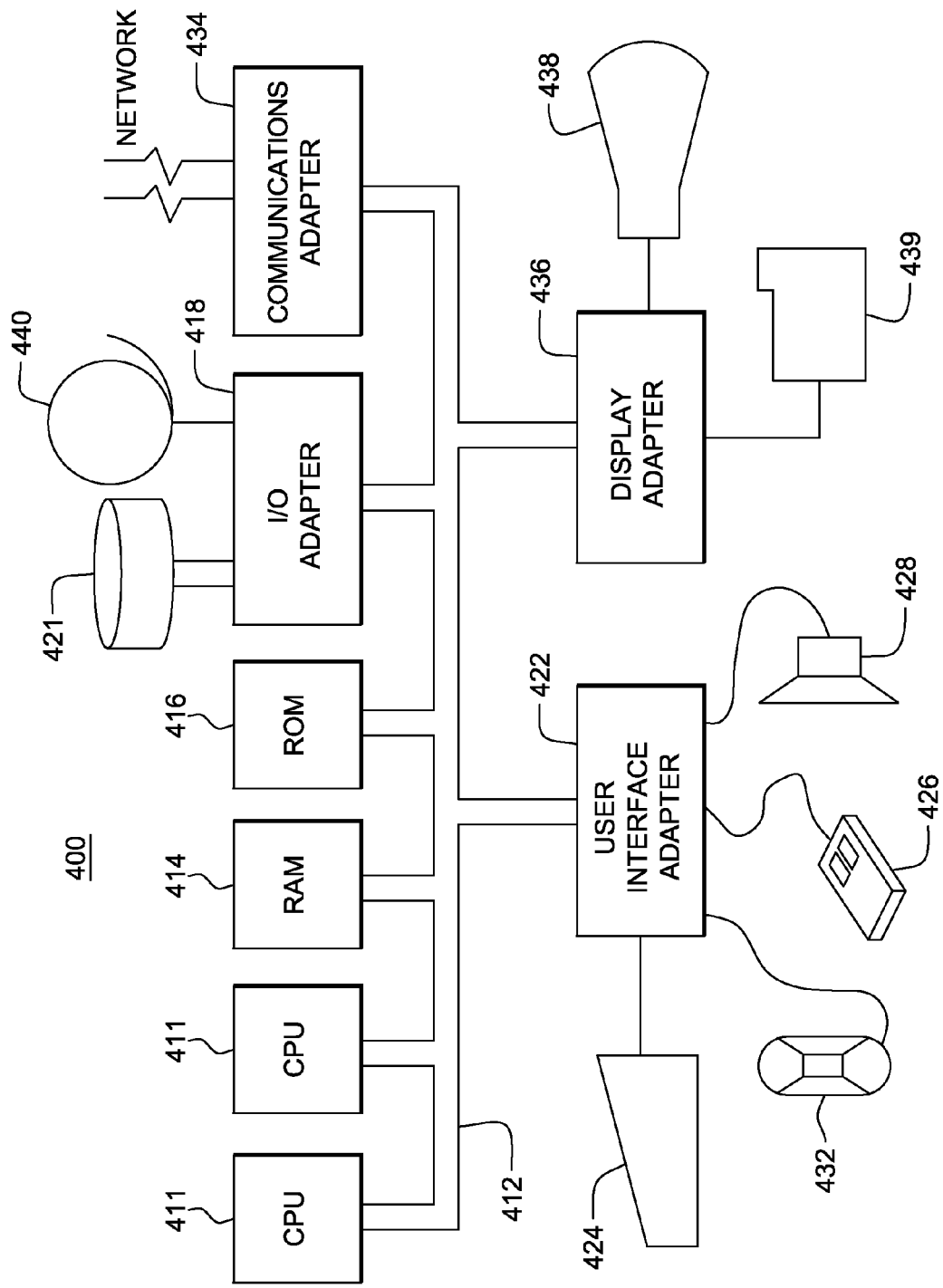

FIG. 6 illustrates an exemplary hardware configuration of a computing system 400 running and/or implementing the method steps described herein with respect to FIGS. 3A,-3B, 4. The hardware configuration preferably has at least one processor or central processing unit (CPU) 411. The CPUs 411 are interconnected via a system bus 412 to a random access memory (RAM) 414, read-only memory (ROM) 416, input/output (I/O) adapter 418 (for connecting peripheral devices such as disk units 421 and tape drives 440 to the bus 412), user interface adapter 422 (for connecting a keyboard 424, mouse 426, speaker 428, microphone 432, and/or other user interface device to the bus 412), a communication adapter 434 for connecting the system 400 to a data processing network, the Internet, an Intranet, a local area network (LAN), etc., and a display adapter 436 for connecting the bus 412 to a display device 438 and/or printer 439 (e.g., a digital printer of the like).

As will be appreciated by one skilled in the art, embodiments of the present disclosure may be embodied as a system, method or computer program product. Accordingly, embodiments of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with a system, apparatus, or device running an instruction.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with a system, apparatus, or device running an instruction. Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may run entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described below with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which run via the processor of the computer or other programmable data processing apparatus, create means for implementing the functions/acts specified in the flowchart and/or block diagram block or blocks. These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which run on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more operable instructions for implementing the specified logical function(s). It should also be noted that, in some alternative implementations, the functions noted in the block may occur out of the order noted in the figures. For example, two blocks shown in succession may, in fact, be run substantially concurrently, or the blocks may sometimes be run in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While there has been shown and described what is considered to be preferred embodiments of the disclosure, it will, of course, be understood that various modifications and changes in form or detail could readily be made without departing from the spirit of the disclosure. It is therefore intended that the scope of the disclosure not be limited to the exact forms described and illustrated, but should be construed to cover all modifications that may fall within the scope of the appended claims.

What is claimed is:

1. A corrosion measurement apparatus comprising:
   a structure forming an enclosure having a first end and a second end;
   a corrosion sensor device located within said enclosure;
   a first sensor device located within said enclosure for determining a respective air flow value within said enclosure;
   a second sensor device located within said enclosure for determining an air temperature value within said enclosure;
   a third sensor device located within the enclosure for determining an air humidity value within said enclosure;
   a fan device located at the first end of said structure;
   a heating device located within said enclosure; and
   a control device operatively connected with said fan device and heating device for receiving real-time air flow and air temperature values, and air humidity value, and, responsive to said values, said control device generating one or more control signals for modifying operation of at least one of said heating device or fan device, to provide a target uniform temperature and a target air flow within said enclosure while obtaining a corrosion rate measurement via said corrosion sensor device.

2. The corrosion measurement apparatus as in claim 1, wherein said control device is one of: a P-I-D (proportional-integral-derivative) feedback controller, an optimal controller; a model predictive controller; a robust control device or an adaptive control device.

3. The corrosion measurement apparatus as in claim 1, wherein said second sensor device is a temperature sensor for determining a temperature measurement value within said enclosure.

4. The corrosion measurement apparatus as in claim 1, wherein said first sensor device is an air flow sensor for determining an air flow measurement value within said enclosure.

5. The corrosion measurement apparatus as in claim 1, wherein said first sensor device is a differential air pressure sensor for determining said air flow value within said enclosure, said corrosion detection device further comprising:
   a first tube extension having a first end connecting said enclosure at a first location;
   a second tube extension having a first end connecting said enclosure at a second location, an interior of each said first and second tube extensions communicating with an interior of said enclosure,
   wherein said differential air pressure sensor operatively connects a second end of each first and second tube extensions for sensing air pressure differential within said enclosure between said first and second locations.

6. The corrosion measurement apparatus as in claim 1, wherein said third sensor located within said enclosure is a relative humidity sensor for sensing a relative humidity value within said enclosure; and
   a further control device in operative communication with said third sensor to receive real-time humidity value signals and operatively controls one of: a humidifier device or said heating device for adjusting moisture content for air to a target value within said enclosure according to a sensed humidity level within said enclosure.

7. The corrosion measurement apparatus as in claim 3, wherein air flows within said Enclosure interior from said fan device at said first end to said second end of said structure, said temperature sensor located downstream from and behind said heating device such that air speed/volume and temperature is constant within the enclosure.

8. The corrosion measurement apparatus as in claim 7, wherein said heating device is located proximate to or attached to a back of said corrosion sensor device and adjusted to maintain said corrosion sensor device within said enclosure at constant temperature.

9. The corrosion measurement apparatus as in claim 5, wherein said corrosion sensor device is mounted on an interior surface of said enclosure between said first and second locations corresponding to said first and second tube extensions.

10. A method for real-time corrosion measurement in a corrosive atmospheric environment, said method comprising:
providing a corrosion measurement apparatus having a structure forming an enclosure having a first end and a second end, said detection device further comprising:
a corrosion sensor device located within said enclosure;
a first sensor device located within said enclosure for determining a respective air flow value within said enclosure;
a second sensor device located within said enclosure for determining an air temperature value within said enclosure;
a third sensor device located within the enclosure for determining an air humidity value within said enclosure;
a fan device located at the first end of said structure;
a heating device located within said enclosure; and
a control device operatively connected with said fan device and heating device for receiving real-time air flow and air temperature values, and air humidity value; and,
generating, by said control device, responsive to said values, one or more control signals for modifying operation of one or more of said heating device or said fan device to achieve a target air temperature and a target uniform air flow within said enclosure; and,
obtaining, via said corrosion sensor device, a corrosion rate measurement while said target air temperature and a target uniform air flow values are achieved within said enclosure.

11. The method as claimed in claim 10, wherein said control device is one of: a P-I-D (proportional-integral-derivative) feedback controller, an optimal controller; a model predictive controller; a robust control device or an adaptive control device.

12. The method as claimed in claim 10, wherein said first sensor device is one of: an air flow sensor or a differential air pressure sensor for determining an air flow measurement value within said enclosure; and
said second sensor device is a temperature sensor for determining a temperature measurement value within said enclosure.

13. The method as claimed in claim 12, wherein said differential air pressure sensor operatively connects said enclosure between first and second locations for sensing an air pressure differential within said enclosure, said corrosion sensor device is mounted on an interior surface of said enclosure between said first and second locations.

14. The method as claimed in claim 10, wherein said third sensor device is a relative humidity sensor for determining the moisture content value within the enclosure, said method further comprising:
providing a further control device in operative communication with said third sensor device;
receiving, at said further control device, real-time humidity value signals; and
controlling, by said further control device, one of: a humidifier device or said heating device for adjusting air moisture content within said enclosure to a target humidity value according to received humidity value signals.

15. The method as claimed in claim 14, further comprising:
providing a plurality of said corrosion measurement apparatuses at one or a plurality of environments, each of said plurality of devices having a common condition of said target air flow, air humidity and target air temperature values within said enclosure at each said one or plurality of environments; and,
obtaining a corrosion rate measurement using said corrosion sensor device of said corrosion measurement apparatus at each said one or plurality of environments when said common target air conditions are achieved at each said device.

16. A method for real-time corrosion detection in corrosive atmospheric environments, said method comprising:
providing a plurality of real-time corrosion measurement apparatuses at one or more environments, each corrosion measurement apparatus comprising:
a structure forming an enclosure having a first end and a second end;
a corrosion sensor device mounted within said enclosure;
a first sensor device located within said enclosure for determining a respective air flow value within said enclosure;
a second sensor device located within said enclosure for determining an air temperature value within said enclosure;
a third sensor device located within the enclosure for determining an air humidity value within said enclosure;
a fan device located at a first end of said structure;
a heating device located within said enclosure; and,
a control device operatively connected with said fan device and heating device to receive real-time air flow and air temperature values, and air humidity value from said enclosure, and generate, responsive to said values, one or more control signals for modifying operation of one or more of said heating device or said fan device;
providing, using said control signals at each respective measurement apparatus of said plurality of corrosion measurement apparatuses, a common condition of a target air flow and target air temperature values within said enclosure of each said corrosion measurement apparatus at each said one or more environments; and,
obtaining, via said corrosion sensor device of each corrosion measurement apparatus, a corrosion rate measurement while said common condition is provided within said enclosure at each respective one or more environments.

17. The method as claimed in claim 16, wherein said one or more environments are at geographically disperse locations.

18. The method as claimed in claim 16, wherein said one or more environments are located in a single geographical location.

19. The method as claimed in claim 16, wherein said one or more environments includes an information technology data center.

20. The method as claimed in claim 16, wherein said first sensor device is one of: an air flow sensor or a differential air pressure sensor for determining an air flow measurement value within said enclosure; and
said second sensor device is a temperature sensor for determining a temperature measurement value within said enclosure; and said third sensor device is a relative humidity sensor for determining the moisture content within said enclosure.

21. The method as claimed in claim 20, wherein said differential air pressure sensor operatively connects said enclosure between first and second locations for sensing an air pressure differential within said enclosure, said corrosion measurement apparatus is mounted on an interior surface of said enclosure between said first and second locations.

22. The method as claimed in claim 16, wherein each corrosion measurement apparatus further comprises: a further control device in operative communication with said third sensor device, wherein said providing a common condition within each said plurality of corrosion measurement apparatuses at each said one or more environments further comprises:
receiving, at said further control device, real-time humidity value signals; and
controlling, by said further control device, one of: a humidifier device or said heating device for adjusting air moisture content within said enclosure of each measurement apparatus to a target humidity value according to received humidity value signals,
said corrosion rate measurement obtained at each detection device while at said target humidity value within said enclosure.

23. The method as claimed in claim 16, further including: setting a target air temperature value and a target uniform air flow value at each said corrosion measurement apparatus at each said one or more locations.

24. A computer program product for providing real-time corrosion measurement in corrosive atmospheric environments, the computer program product comprising a tangible, non-transitory, storage medium readable by a processing circuit and storing instructions run by the processing circuit for performing a method, wherein a plurality of real-time corrosion measurement apparatuses are located at one or more environments,
each corrosion measurement apparatus comprising:
a structure forming an enclosure having a first end and a second end;
a corrosion sensor device mounted within said enclosure;
a first sensor device located within said enclosure for determining a respective air flow value within said enclosure;
a second sensor device located within said enclosure for determining an air temperature value within said enclosure;
a third sensor device located within the enclosure for determining an air humidity value within said enclosure;
a fan device located at a first end of said structure;
a heating device located within said enclosure; and,
a control device operatively connected with said fan device and heating device to receive real-time air flow and air temperature values, and air humidity value, and generate, responsive to said values, one or more control signals for modifying operation of one or more of said heating device or said fan device; and,
said method comprising:
providing, using said control signals at each respective measurement apparatus of said plurality of measurement apparatuses, a common condition of a target air flow and target air temperature values within said enclosure of each said measurement apparatus at each said one or more environments; and,
obtaining, via said corrosion sensor device of each detection measurement apparatus, a corrosion rate measurement while said common conditions are provided within said enclosure at each respective one or more environments.

25. The computer program product as claimed in claim 24, wherein said first sensor device is one of: an air flow sensor or a differential air pressure sensor for determining an air flow measurement value within said enclosure; and
said second sensor device is a temperature sensor for determining a temperature measurement value within said enclosure; and, said the third sensor device that is a relative humidity sensor for determining the moisture content within said enclosure 26. The computer program product as claimed in claim 24, wherein each corrosion measurement apparatus further comprises: a further control device in operative communication with said third sensor device, wherein said providing a common condition within each said plurality of corrosion measurement apparatuses at each said one or more environments further comprises:
receiving, at said further control device, real-time humidity value signals; and
controlling, by said further control device, one of: a humidifier device or said heating device for adjusting air moisture content within said enclosure of each measurement apparatus to a target humidity value according to received humidity value signals,
said corrosion rate measurement obtained at each detection device while at said target humidity value within said enclosure.

27. The computer program product as claimed in claim 24, wherein the method further includes: setting a target air temperature value and a target uniform air flow value at each said device at each said one or more locations.

* * * * *